United States Patent [19]
North et al.

[11] Patent Number: 5,221,457
[45] Date of Patent: Jun. 22, 1993

[54] SYSTEM FOR ANALYZING ION LEVELS IN FLUIDS

[75] Inventors: John R. North, Agoura Hills; Robert L. Kay, Thousand Oaks, both of Calif.; Jeff Brown, Seattle, Wash.; Mark Eike, Aliso Viejo; Neil Plotkin, Pasadena, both of Calif.

[73] Assignee: Porton Diagnostics, Inc., Westlake Village, Calif.

[21] Appl. No.: 763,696

[22] Filed: Sep. 23, 1991

[51] Int. Cl.$^5$ .................................................. G01N 27/333
[52] U.S. Cl. ..................................... 204/416; 204/400; 204/418
[58] Field of Search ............... 204/400, 416, 418, 419, 204/420, 435

[56] References Cited

U.S. PATENT DOCUMENTS

| | | | |
|---|---|---|---|
| 4,654,127 | 3/1987 | Baker et al. | 204/416 |
| 4,929,426 | 9/1990 | Bodai et al. | 204/419 |

Primary Examiner—T. Tung
Attorney, Agent, or Firm—Kenyon & Kenyon

[57] ABSTRACT

A system for analyzing the ion level of a fluid sample including an analyzer instrument, containing electrical circuitry for analyzing the ion level of the fluid sample, in electrical communication with a sensor unit having an ion selective electrode in communication with the fluid sample and electrical contacts for communication with the analyzer instrument. A recharger unit for the analyzer instrument is also disclosed.

22 Claims, 14 Drawing Sheets

SYSTEM FOR ANALYZING ION LEVELS IN FLUIDS

FIELD OF THE INVENTION

The present invention relates to a system for use in analyzing the ion content of fluid samples, particularly blood samples. The system comprises a sensor portion, with an ion sensitive electrode, adapted to slide into an analyzer instrument that contains circuitry for analyzing the ion level of the fluid sample. The system also includes a base portion for storing and recharging the analyzer instrument.

BACKGROUND OF THE INVENTION

Ion sensitive electrodes are generally utilized in the medical field to detect ion levels in fluids. Typically, these electrodes detect ion levels by measuring the electrical potential (EMF—electromotive force) generated across a membrane separating two solutions with different concentrations of ions. Alternatively, a nonporous, electrically non-conductive film, such as polyvinyl chloride, impregnated with an ionophore specific to the ion to be measured can be employed. In the absence of the ionophore, the film is an insulator and no EMF can be measured across the film, When the film is blended with an ionophore, charged ions are bound to the film and a small, measurable current can be induced to flow. Because the ionophore is selective in its affinity, and thus will bind only certain specific ions, such electrodes are ion selective. Any measurable EMF is due solely to the presence of the bound ions.

Generally, ion sensitive electrodes are used in conjunction with an analyzer instrument as part of a diagnostic system. Examples of disposable ion sensitive electrode sensors are disclosed in U.S. patent application Ser. No. 07/745,971 entitled "Method and Apparatus for Single Determination Blood Analysis", and U.S. patent application Ser. No. 07/220,246 entitled "Precalibrated, Disposable Electrochemical Sensors", now abandoned. The disclosure of each of these patent applications is incorporated herein by reference.

The system may contain a sensor portion, that may be disposable, that places a fluid, such as blood, in contact with the ion sensitive electrode. After the fluid has been placed in contact with the ion sensitive electrode, the analyzer instrument portion of the system, containing electrical circuitry, analyzes the ion level of the fluid. For example, in the case of a blood sample, the potassium ion level may be measured.

Diagnostic systems wherein the sensor portion and the analyzer instrument are part of a single unit are generally known. Systems having a disposable (single use) sensor portion adapted to communicate with a non-disposable analyzer instrument are also generally known. Existing design of disposable, single use ion selective electrode sensors calls for the disposable potentiometric sensing elements to be mounted on an electrically non-conductive support that is inserted into the re-usable analyzer instrument for analysis of the potentiometric electronic signals and thereby the ion level of the sample. The electrical signals transmitted between disposable sensor and the analyzer instrument are characteristically of low current and low direct voltage and are therefore susceptible to electronic noise and to poor electrical contacts in the measurement circuit.

Additionally, in generally known systems, in order to ensure good electrical contact between the conductive elements of the sensor and the analyzer instrument, a sliding movement is utilized during the insertion of the disposable sensor portion into the analyzer instrument. This sliding movement, in generally known systems, causes the non-conductive support of the sensor portion to slide against a non-conductive part of the analyzing instrument. This relative movement of the two non-conductive parts generally causes significant errors in the potentiometric measurement due to the generation of static electrical charges and associated electrical fields.

Further, in generally known systems, the sensor portion is exposed, at least in part, after it has been connected to the analyzer instrument. Thus, the ion selective electrode, and the contact electrodes between the sensor portion and analyzer instrument are at least partially exposed to external electrical fields. These external electrical fields may cause errors in the measurement of the ion level of the fluid sample.

The foregoing disadvantages of heretofore generally known systems are overcome, and additional advantages achieved by the system of the present invention.

SUMMARY OF THE INVENTION

The system of the present invention comprises an analyzer instrument, containing electrical circuitry for analyzing the ion level of a fluid sample, that electrically communicates with a sensor unit having an ion sensitive electrode and electrical contacts for communication with the analyzer instrument. The system of the present invention may also include, if the analyzer unit is powered using rechargeable batteries, a recharger unit that additionally serves as a base stand for the analyzer instrument. The component parts of the system of the present invention are described in further detail below.

THE SENSOR UNIT

The sensor unit is adapted to be inserted into the analyzer instrument and includes an ion selective electrode and electrical contacts for communication with electrical contacts in the analyzer instrument. The sensor unit may be equipped with an adhesive or directly printed label, such as a bar code label. The label may contain various information, such as, for example, the identification of the response characteristics of the ion selective membrane. The leading edge of the sensor unit may be adapted to facilitate the insertion of the sensor unit into the analyzer instrument and the trailing edge of the sensor unit may be adapted to facilitate the holding of the sensor unit in the hand of a user of the system. The leading edge of the sensor unit refers to the edge first inserted into the analyzer instrument, and the trailing edge refers to the edge opposite the leading edge. The sensor unit may additionally include a notch, or other means for mechanically engaging the analyzer instrument, when the sensor unit has been fully inserted into the analyzer instrument.

According to the present invention, the sensor unit, comprises an ion sensitive electrode, preferably mounted on the upper surface of the sensor unit. The sensor unit, on the side opposite the ion selective electrode, may include up to three planar surfaces: a surface for supporting the electrical contacts, a surface for carrying an adhesive or directly printed label and a surface for sliding on an analyzer instrument surface when the sensor is inserted into the analyzer instrument. The surface carrying the electrical contacts may be below the surface carrying the label and the surface for sliding may be below both of the other surfaces so that as the sensor unit is slid into the analyzer, the only contact between the analyzer and the sensor unit, until electrical communication is established, occurs along the sliding surface.

The electrical contacts in the analyzer instrument which correspond to the electrical contacts of the sensor unit, may be resiliently, or depressibly mounted in a surface of the analyzer instrument. The resilient or depressible means that allow movement of the electrical contacts may be springs or other means known in the mechanical arts. The surface of the sensor unit carrying the electrical contacts may be a platform, projecting below the surface of the sensor unit carrying the label. This platform may be adapted to include ramps, disposed towards the leading edge of the sensor unit, in front of the electrical contacts for the purpose of depressing each of the corresponding electrical contacts on the surface of the analyzer instrument as the sensor unit is being inserted into the analyzer instrument. The electrical contacts of the analyzer instrument are depressed by the ramps until the electrical contacts on the sensor unit are over the corresponding electrical contacts in the analyzer instrument. This feature promotes strong compressive contact between each pair of sensor and analyzer electrical contacts, while reducing the conductive area of each of the contacts and only requiring relative movement between the analyzer instrument and sensor unit in a single plane. This feature also increases the non-conductive path between the contacts in the sensor unit and the contacts in the analyzer instrument thereby enhancing the electrical insulation between the contacts.

The ramps also allow smooth transition of the electrical contacts, in both the sensor unit and the analyzer instrument, between "at rest" and "sliding" states. This minimizes lateral forces on the analyzer contacts at the points when the sliding sensor unit first touches each of the analyzer contact, and reduces, or eliminates physical resistance in the movement of the sensor unit into the analyzer instrument. The reduction in physical resistance advantageously increases the reliability of the reading of the sensor unit's bar code by the analyzer instrument.

The label on the sensor unit may contain information that can be read by a user of the system as well as bar code, or similar information, that may be scanned and read by a bar code, or similar, reader in the analyzer instrument during insertion of the sensor unit into the analyzer instrument. In the embodiment of the present invention wherein the electrical contacts of the sensor unit are part of a planar surface projecting below the label carrying surface, the label may be shaped or adapted to fit around the projecting surface carrying the electrical contacts.

The ion sensitive electrode used in sensor unit may be any ion sensitive electrode conventionally utilized for the measurement of ion levels in a fluid such as the ion sensitive electrode disclosed in U.S. patent application Ser. No. 07/745,971. The ion sensitive electrode may be precalibrated using a hydrogel as described in U.S. patent application Ser. No. 07/220,246. (The disclosure of each of these patent applications has been incorporated by reference above.) As will be understood by those of ordinary skill in the art, a fluid sample is placed in contact with the ion sensitive electrode to determine the ion level in the sample.

According to the present invention, the ion sensitive electrode may be covered with a hydrogel, containing known amounts of electrolytes, for precalibration before use. Suitable hydrogels, and their use in precalibrating are known to those of ordinary skill in the art and include acrylamide hydrogel. Suitable hydrogels, and their use, are also described in U.S. patent application Ser. No. 07/220,246. A peel-off cap may be provided over the hydrogel, to act as a moisture barrier and thereby prevent evaporation of the hydrogel. We have discovered that when the peel-off cap is formed from a polymer-coated aluminum sheet, the peel-off cap will adhere to the hydrogel without an adhesive or support matrix. Thus, preferably the peel-off cap is formed from a polymer-coated aluminum sheet that, in addition to acting as a moisture barrier, pulls the hydrogel off the ion sensitive electrode, as the cap is peeled away from the ion sensitive electrode. In this manner, peeling the cap off the ion sensitive electrode removes the hydrogel and exposes the electrode for sample deposition. A further advantage of the polymer-coated aluminum cap is that the cap generally will not react electrochemically with salt solutions in the hydrogel.

The sensor unit may additionally contain means for engaging actuating means located in a receiving portion of the analyzer instrument, when the sensor unit is fully inserted into the analyzer instrument and the electrical contacts of the sensor unit are correctly positioned over corresponding electrical contacts in the analyzer instrument. The means for engaging can comprise, for example, a raised bump on the surface of the sensor unit. The height of the raised bump, however, should be below the height of the sliding surface of the sensor unit.

The sensor unit may be constructed from a variety of plastics or moldable, polymeric materials known to the art. Preferably the sensor unit is constructed from a polyvinyl chloride plastic material. As will be explained in greater detail below, portions of the sensor unit may be coated with an electrically conductive material, or manufactured from an electrically conductive material to minimize reading errors resulting from the generation of static electricity. The sensor unit, with ion selective electrode and electrical contacts, may be fabricated from the polymeric material in manners known to those of ordinary skill in the art.

THE ANALYZER INSTRUMENT

The analyzer instrument of the system of the present invention includes a receiving portion adapted to receive and electrically communicate with the sensor unit, electrical circuitry for analyzing the electrical signals generated by the sensing unit and determining the ion level of the fluid sample, display means for displaying the ion level of the sample and control means for turning the analyzer instrument on and off and thereby starting and stopping the analysis of the fluid sample. Preferably, the electrical circuitry is similar to the circuitry described in U.S. patent application Ser. No. 07/750,534, "Analyzer Circuitry for Analyzing Samples on Ion Sensitive Electrodes" the disclosure of which is incorporated herein by reference.

The receiving portion of the analyzer instrument of the analyzer instrument is adapted to receive the sensor unit and includes electrically conductive pads or contacts for electrically communicating with the sensor unit, a sensor slide surface, means for guiding the sensor unit and actuating means for activating the analyzer instrument upon complete insertion of the sensor unit.

In the embodiment of the present invention wherein the sensor unit contains a bar code label, the receiving portion of the analyzer instrument includes a bar code reader for scanning the bar code as the sensor unit is inserted into the analyzer instrument. The receiving portion of the analyzer instrument may also include mechanical means for engaging the notch or similar means in the sensor unit, to stop the movement of the sensor unit into the analyzer instrument when the electrical contacts of the sensor units are positioned over the electrically conductive pads, or contacts, in the receiving portion of the analyzer instrument. By way of example, these mechanical means may comprise detent springs.

The electrically conductive pads, or contacts, in the receiving portion of the analyzer instrument make contact with the electrical contacts of the sensor unit to transmit the electronic output signals of the sensor unit. Preferably, the electrically conductive pads are able to move independently of each other in a plane perpendicular to the plane of movement of the sensor unit during its insertion or removal. In order to protect, and seal, the internal portions of the analyzer instrument containing the analyzer circuitry, the electrically conductive pads are preferably mounted in an electrically insulating elastomeric part of the receiving portion. Mounting the electrical pads in this way also advantageously permits cleaning of the conductive pads and their surrounding surfaces and the receiving portion of the analyzer instrument. The elastomer also protects the means for moving, and controlling the movement of the individual pads, from the environment. These means for moving may be springs or similar means generally utilized in the mechanical arts.

The sensor slide surface of the receiving portion is a surface adapted to contact the raised sliding surface of the sensor unit. The guiding means of the receiving portion may comprise planar surfaces, perpendicular to the sensor slide surface, that engage the side edges of the sensor unit. The guiding means may also include, or comprise, detent springs that bear down on the top portion of the sensor unit and/or engage notches in the sensor unit. The guiding means may also control the movement of the sensor unit into the receiving portion by bearing on the sensor unit as it is slid into the analyzer thereby resulting in a friction control on the sensor unit's movement and pressing the sensor unit towards the electrical contacts in the receiving portion. Preferably the sensor slide surface and the guiding means are coated with a hard wearing electroconductive material such as a thin film of metal which is electrically connected to the ground plane of the printed circuit assembly, containing the analyzer circuitry, so that an electroconductive path is formed between these surfaces and the ground plane of the printed circuit assembly within the analyzer instrument. Alternatively, the sensor slide surface and the guiding means may be manufactured from an electroconductive material, such as a carbon filled, or metal filled, molded plastic or a diecast metal, to allow the formation of the electroconductive path. The electroconductive path advantageously reduces the formation of static electrical charge during the sliding insertion of the sensor unit into the analyzer instrument and also serves to drain any static electrical charge that is formed away from the measurement circuits of the analyzer instrument to reduce errors in the measurement of the ion level of the sample.

The sensor slide surface and guiding means may be incorporated into a removable analyzer slide that may be removed from the analyzer instrument to facilitate cleaning. The analyzer slide may additionally include the mechanical means, such as detent springs, for stopping the movement of the sensor unit into the analyzer. These means may also control the movement of the sensor unit into the analyzer slide by bearing on the sensor unit as it is slid into the analyzer thereby resulting in a friction control on the sensor unit's movement and pressing the sensor unit towards the electrical contacts in the receiving portion. The analyzer slide may also include mechanical means, such as detent springs corresponding to notches in the analyzer instrument receiving portion, for locating and positioning the analyzer slide in the receiving portion.

The actuating means of the receiving portion comprises an electrical switch, or similar means, in electrical communication with the analyzer circuitry. Preferably, the actuating means are mounted in an elastomeric membrane to protect the internal environment of the analyzer instrument from contamination. The actuating means are mechanically engaged, by the means for engaging on the sensor unit, when the sensor unit is fully inserted into the receiving portion. The mechanical engagement of the actuating means changes the state of a microswitch, or similar means, in the analyzer circuitry of the analyzer instrument. In this manner the actuating means communicates to the analyzer circuitry that a sensor unit is in position to be analyzed.

The receiving portion of the analyzer instrument may be covered with a slidable or removable cover for protection. The cover may comprise a slidable, or removable, door. In the "open" position the door is slid to one side, or removed, to allow the sensor unit to be inserted into the receiving portion. After insertion of the sensor unit into the receiving portion the cover is slid to the "closed" position, or replaced, to shield and protect the sensor unit and/or the receiving portion of the analyzer instrument. The sensor unit and receiving portion are adapted so that after the sensor unit is fully inserted into the receiving portion the sensor unit is fully enclosed when the cover is in the closed position.

Preferably, the cover, and the walls, of the receiving portion are formed from a material that provides electrostatic discharge (ESD) and electromagnetic (EMI) shielding properties. The cover, or door, may be such that when in the "closed" position there is no gap in the ESD or EMI shield greater than 0.5 inch and such that the cover, or door, is in continual low resistance electrical connectivity with the ground plane of the analyzer circuitry. In the case of a door, this electrically connectivity may be achieved through the door's pivot.

In a preferred embodiment of the present invention, a door is utilized to provide ESD and EMI shielding. The door is removable to facilitate cleaning and repair by removal of a single pivot screw. Electrical connectivity between the door and the analyzer circuitry is achieved without additional washers or wires, and without reliance on thread to thread contact between the screw and the analyzer housing, by providing a raised sliding contact, in the analyzer housing, surrounding the pivot screw, or a series of raised conductive pads, in the analyzer housing, disposed in a circle surrounding the pivot screw. The sliding contact or conductive pads may be placed in compressive contact with a circular conductive area of the door surrounding the screw. The compression may be maintained by providing shoulders on the screw that prevent over tightening.

The door assembly also preferably includes electrical contacts for contacting the corresponding electrical contacts in the analyzer instrument housing when the door is in the closed position. The electrical contacts in the analyzer instrument housing electrically communicate with the analyzer circuitry to allow the circuitry to detect when the door is fully closed. Suitable electrical contact include, but are not limited to, a pair of electroconductive pads on the surface of the analyzer instrument housing and a electroconductive bar on the interior of the door disposed such that when the door is in any position other than fully closed, the electroconductive bar does not touch both of the electroconductive pads.

The electrical circuitry utilized in the analyzer instrument to analyze the electrical output signals of the ion sensitive electrode of the sensor unit and thereby determine the ion level, or concentration of the fluid sample, may be similar to the electrical circuitry utilized in ion level analyzers known to the art. Particularly advantageous electrical circuitry is described in the commonly assigned, co-pending, U.S. patent application Ser. No. 07/750,534, "Analyzer Circuitry for Analyzing Samples on Ion Sensitive Electrodes", the disclosure of which is hereby incorporated by reference. The analyzer circuitry may be electrically connected to the electrical pads of the receiving portion, the activation means, the display means, the on/off switching means and a power source in a conventional manner.

The display means and means for electrically switching the analyzer on and off may be any means known to those of ordinary skill in the art. For example, the display means may comprise an L.E.D. or L.C.D. display and the switching means may comprise push button switches. The display means, and switching means electrically communicate with the analyzer circuitry. As will be understood by those of ordinary skill in the art, the displays means may display alphanumeric characters and thereby be utilized to provide a sequence of instructions to a user of the analyzer instrument. The display means may also be utilized to display the ion level of the fluid sample being analyzed.

The power source for the analyzer instrument may be any conventional power source. Generally, the analyzer circuits are designed to receive a source of DC power, for example a battery. However, as will be understood by those of ordinary skill in the art, analyzer circuitry may be designed to operate from an AC power source, or designed with an AC/DC transformer to convert alternating current from a power source to direct current to run the analyzer circuitry. In a preferred embodiment of the present invention, the power source for the analyzer instrument comprises rechargeable batteries, such as nickel-cadmium (Ni-Cad) batteries. In this embodiment, the analyzer instrument is adapted for insertion into a recharger unit and the housing of the analyzer instrument contains electrical contacts for electrical communication between the rechargeable batteries and the recharger unit. Preferably these electrical contacts are recessed into the analyzer instrument housing to reduce the chance of accidental electrical connections being formed between contacts.

The recharger unit is adapted to hold the analyzer instrument during the period of recharging and when the analyzer instrument is not be used. The recharger unit comprises means for connecting the recharger unit to a source of AC power, recharger circuitry and electrical contacts for communicating with the electrical contacts in the analyzer instrument housing. The recharger circuitry may be any conventional circuitry for recharging DC batteries using power from an AC power source. When the analyzer instrument is placed in the recharger unit, the electrical contacts in the analyzer instrument contact the electrical contacts in the recharger unit and complete an electrical pathway between the rechargeable batteries and the recharging circuitry in the recharger unit. If the recharger unit is connected to a source of AC power, recharging of the batteries occurs until the analyzer instrument batteries are fully charged.

The analyzer instrument may be fabricated from conventional moldable plastics or polymeric materials such as polyvinyl chloride or acrylonitrile butadiene styrene (ABS). Preferably, after fabrication, the entire inner surface of the analyzer instrument housing are coated with an electroconductive material, such as sprayed metal, or similar materials known to those of ordinary skill in the art. The housing may be molded in a manner that facilitates the ability of a user to hold the analyzer instrument in their hand. As will be understood by those of ordinary skill in the art, the housing of the analyzer instrument may be fabricated in two halves that are mechanically connected by screws or press-fit together after the internal parts of the analyzer instrument have been set in place. Preferably, an elastomeric seal is utilized between the two halves of the analyzer instrument to seal the analyzer instrument and protect the internal components from moisture.

The door, or cover, over the receiving portion of the analyzer instrument may be similarly constructed from conventional moldable plastics or polymeric materials such as polyvinyl chlorides or ABS. Preferably, after fabrication, the entire inner surface of the door is coated with an electroconductive material, such as sprayed metal, or similar materials known to those of ordinary skill in the art. The door may be fitted and attached to the analyzer instrument housing in a manner that allows the door to rotate between "open" and "closed" positions. Preferably a screw, or similar means, as described above are utilized to attach the door to the analyzer instrument housing.

As discussed in the preceding section we have discovered that the sliding movement of the sensor unit into the analyzer instrument may cause significant errors in the potentiometric measurement due to the generation of static electrical charges and associated electrical fields. In order to avoid this source of errors one of the following embodiments of the sensor unit and analyzer instrument are preferred:

1) a sensor unit and analyzer instrument having conductive surfaces at all positions where the sensor unit makes sliding contact with the analyzer instrument, the conductive surfaces being electrically insulated from the electrical contacts utilized for transmission of potentiometric electronic signals from the sensor unit to the analyzer instrument and being electrically connected to the electronic ground plane of the analyzer instrument when the sensor unit is fully inserted into the analyzer instrument;

2) a sensor unit fabricated from polyvinyl chloride plastic with parts of the analyzer instrument that make sliding contact with the sensor unit, except the electrical contacts, and the area immediately surrounding the electrical contacts, being coated with an electrically conductive material or fabricated from an electrically conductive material wherein the conductive parts of the analyzer instrument are electrically connected to the electronic ground plane of the analyzer instrument and the electrical contacts of the sensor unit, required for transmission of the potentiometric electronic signals from the sensor unit to the analyzer instrument, are electrically insulated from the parts of the sensor unit that make sliding contact with the analyzer instrument. As discussed above, the conductive portions of the analyzer instruments, that make sliding contact with the sensor unit, may be fabricated in a manner that allows for their removal to permit their cleaning or decontamination.

We have also discovered that the magnitude of the electrical resistance of the potentiometric sensing membrane of the ion selective electrode affects the susceptibility of the system to errors caused by the static electrically generated by sliding the sensor unit into the analyzer instrument, or transferred to the sensor unit from other sources of static electricity. Generally, the greater the membrane resistance, measured using a low direct current, the longer the time taken for electrostatic-induced errors to dissipate. Accordingly, a preferred embodiment of the present invention includes a sensing membrane, in the ion selective electrode, with less than 300 MegOhm resistance, measured using a 100 pico amp current, which has a residual error of 250 microvolts after 60 seconds. In situations of use where an ion level measurement is required as soon as possible after insertion of the sensor unit into the analyzer instrument, the sensing membrane preferably has less than 100 MegOhm resistance, measured using a 100 pico amp current, which has a residual error of less than 100 microvolts after 30 seconds.

We have further discovered that the spatial orientation of the electrically conductive pads in the analyzer instrument, that make electrical contact with the sensor unit to effect transmission of the potentiometric electronic signals between the sensor unit and the analyzer instrument, affects the susceptibility of the system to errors arising from static electrical fields generated by relative movement of the sensor unit and the analyzer instrument. Where said relative movement and said electrically conductive pads are both in the horizontal plane, movement-induced errors are greater than when the electrically conductive pads are positioned perpendicular to the plane of movement.

In a preferred embodiment of the present invention, the analyzer instrument housing is manufactured with a size, shape and weight balance suitable for hand-held use. With its door closed, fully enclosing the removable sensor unit, the analyzer instrument forms a complete ESD, EMI shield equivalent to a Faraday cage. The rechargeable batteries permit cordless use. Thus, in this preferred embodiment, the system of the present invention is believed to be the first hand-held, fully shielded, rechargeable battery operated ion selective electrode analyzer.

Additional advantages of the system of the present invention will become apparent from the following more detailed description.

DETAILED DESCRIPTION OF THE INVENTION

A preferred embodiment of the present invention is described in the following paragraphs with reference to the accompanying figures.

Figure 1:
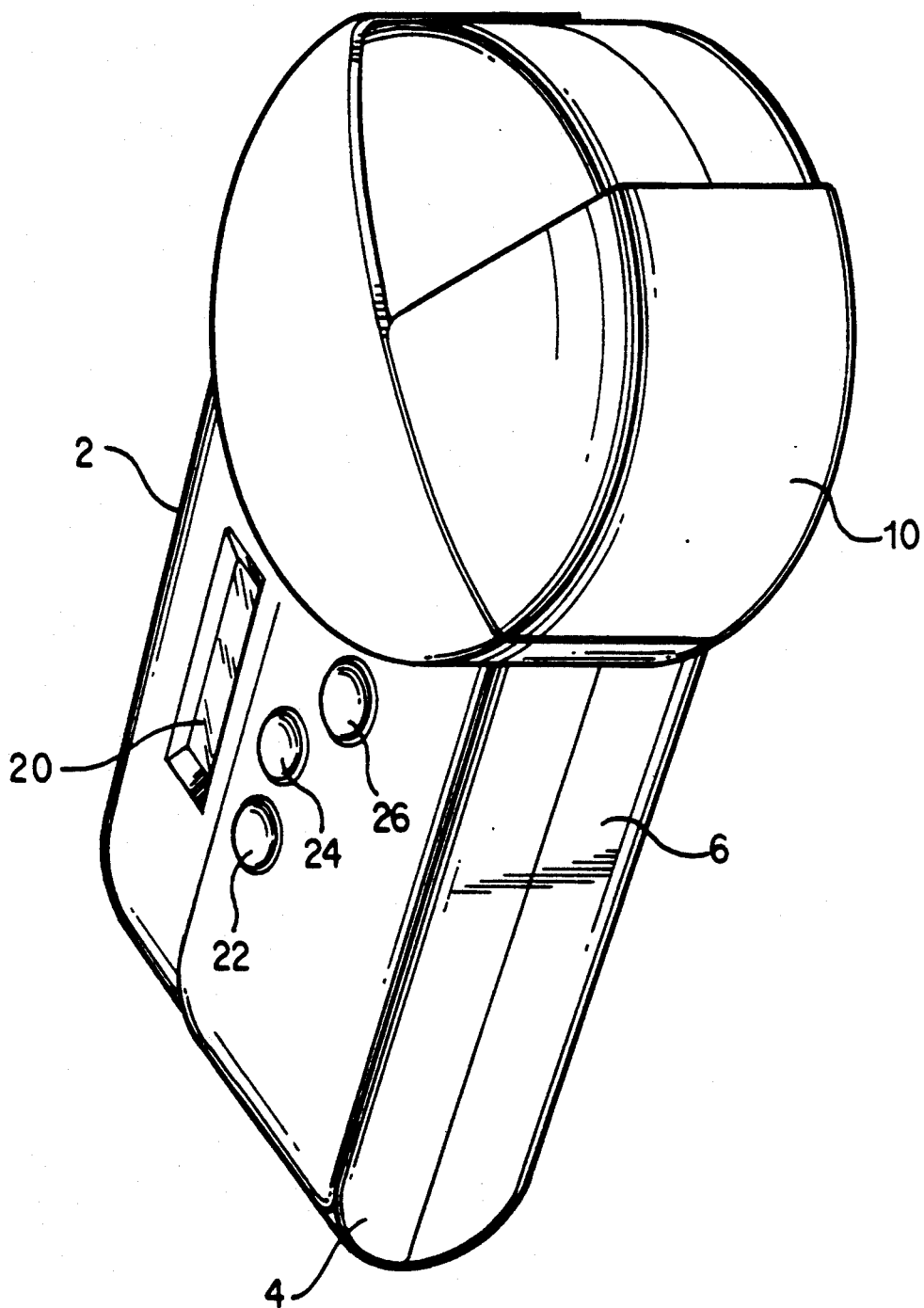
FIG. 1 is a top view of the analyzer instrument of the system of the present invention with its door in the closed position.

FIG. 1 depicts the analyzer instrument 2, of the system of the present invention with cover, or door, 10 in a closed position. The analyzer instrument 2, comprises two halves, top half 4, and bottom half, 6 mechanically connected to form a housing. Display means 20 comprise an LED or LCD display and are utilized to convey information, such as ion level concentration to a user of the system. Button switches, 22, 24 and 26 are user accessible and may be utilized to turn the analyzer instrument on and off, and to control other features of the analyzer instrument.

Figure 2:
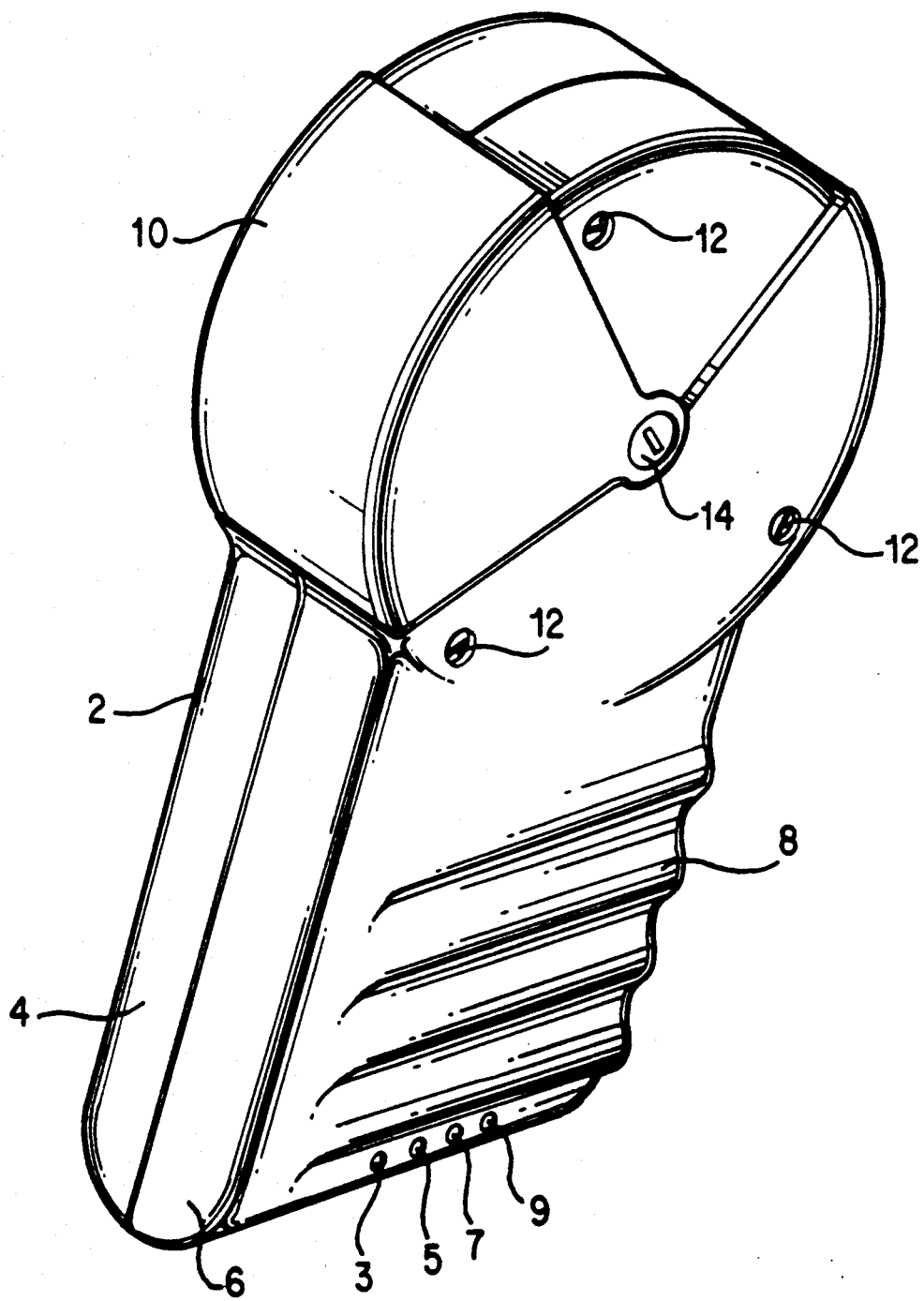
FIG. 2 is a bottom view of the analyzer instrument of the system of the present invention with its door in the closed position.

FIG. 2 depicts the analyzer instrument 2, of the system of the present invention from a bottom view. As shown in FIG. 2, bottom half 6 of the analyzer instrument housing may be molded with ridges 8, that provide a convenient gripping surface for the hand of a user of the analyzer instrument. Fastener means 12, and pivot screw 14, for cover, or door, 10, are shown in the bottom half 6 of the analyzer instrument housing. Fastener means 12 are utilized to fasten the two halves of the analyzer instrument housing together and may additionally be utilized to secure, receiving portion 100, depicted in FIG. 8 to the analyzer housing. Suitable fastener means include screws and rivets. Alternatively, the bottom and top halves of the analyzer instrument may be molded in a manner that permits them to be press fit together. The analyzer instrument housing, may additionally contain electrical contacts 3, 5, 7 and 9 for electrically communicating with a recharger unit to recharge batteries located in the analyzer instrument. Preferably, electrical contacts 3, 5, 7 and 9 are recessed.

Figure 3:
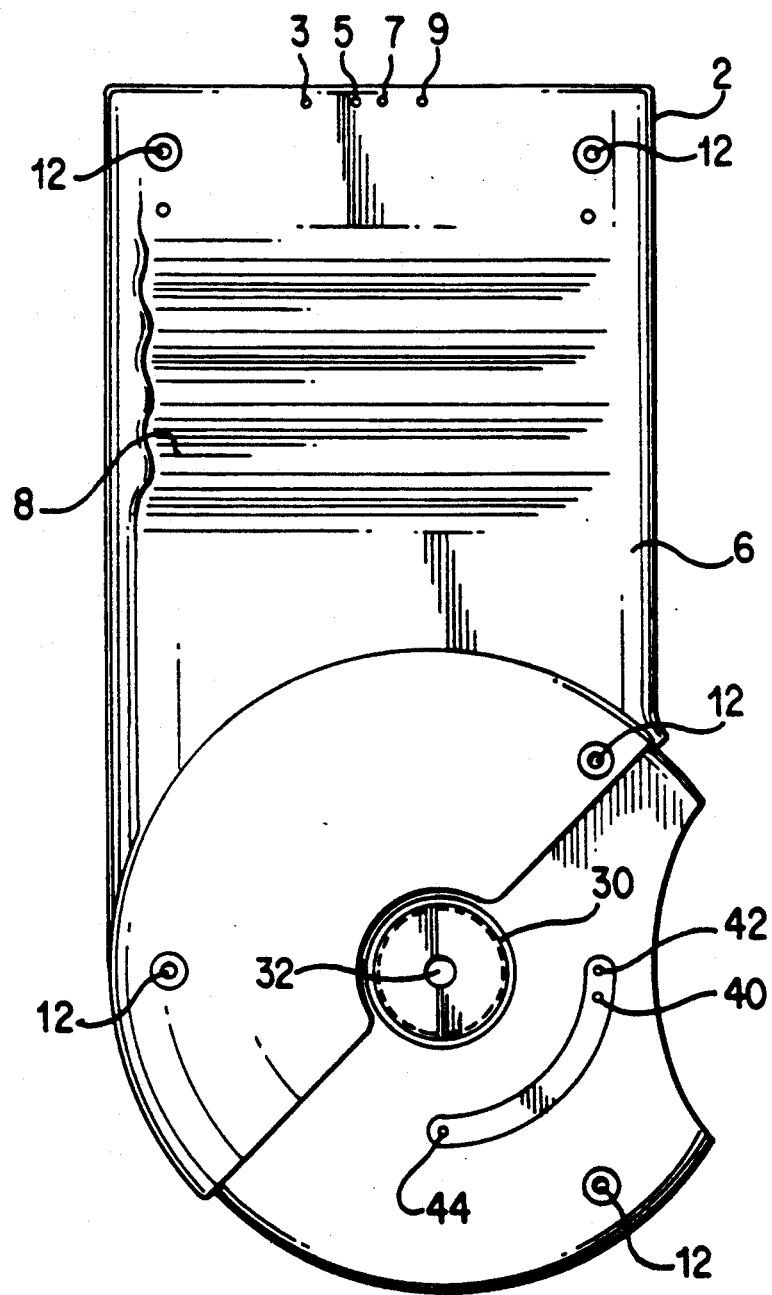
FIG. 3 is a bottom view of the analyzer instrument of the system of the present invention with its door removed.

FIG. 3 depicts a bottom view of a possible embodiment of the analyzer instrument of the system of the present invention without cover 10. In the embodiment depicted in FIG. 3, the attaching means for attaching cover 10 to the analyzer instrument 2, comprise a raised sliding contact 30 surrounding pivot screw hole 32, for establishing electrical connectivity between cover 10 (not shown) and the analyzer instrument 2. FIG. 3, also shows electrically conductive pads 40, 42 and 44 that correspond to a electrically conductive bar portion on cover 10. When the cover is in the fully closed position, the electrically conductive bar covers, and completes an electrical pathway between, pads 40 and 42, that are each electrically connected to the analyzer circuitry. Completion of this electrical pathway informs the analyzer circuitry that the cover is in a fully closed position. Similarly, when the cover is in the open position, the electrically conductive bar covers pad 44 that is electrically connected to the analyzer circuitry, thereby informing the analyzer circuitry that the cover is in the open position. Fastener means 12, are utilized to fasten the two halves of the analyzer instrument housing together and may additionally be utilized to secure, internal components of the analyzer instrument to the instrument's housing. Suitable fastener means include screws and rivets.

Figure 4:
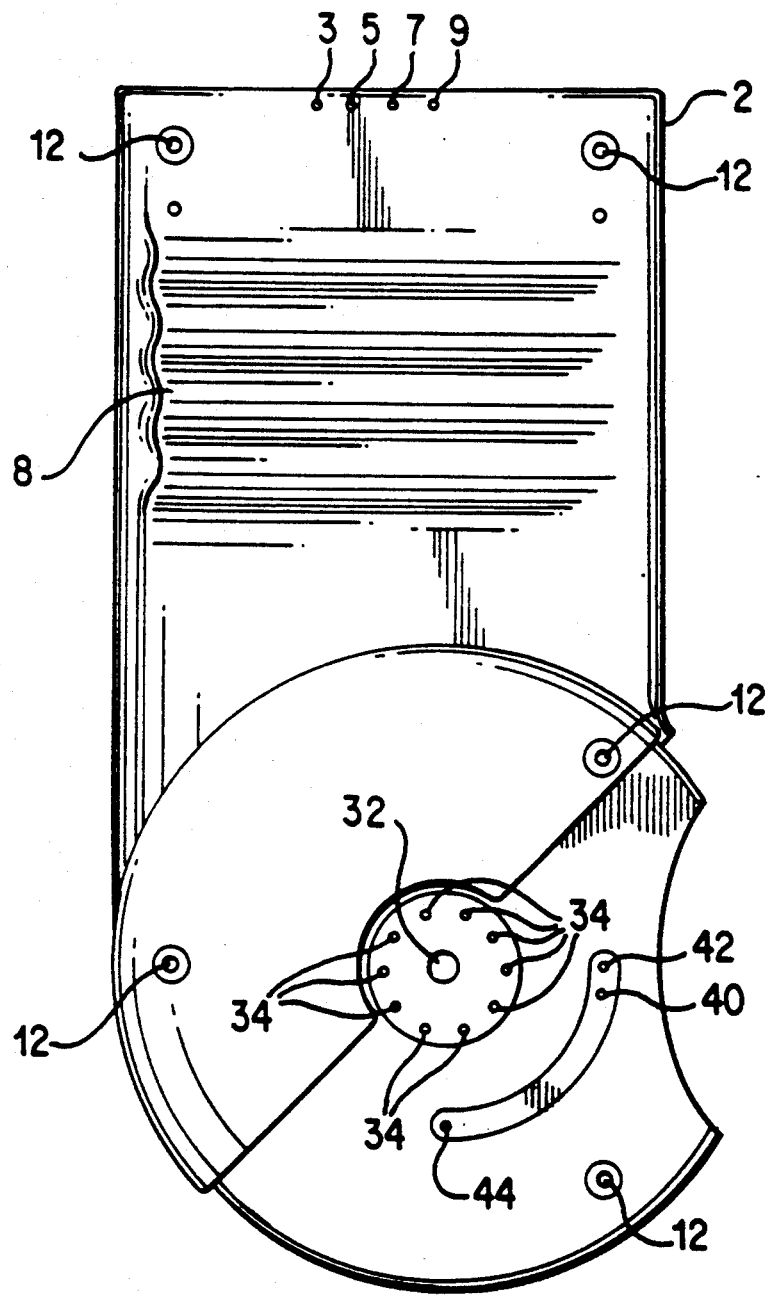
FIG. 4 is a bottom view of the analyzer instrument of the system of the present invention with its door removed.

FIG. 4 depicts a bottom view of an alternative embodiment of the analyzer instrument of the system of the present invention without cover 10. In the embodiment depicted in FIG. 4, the attaching means for attaching cover 10 to the analyzer instrument 2, comprise a raised a series of raised conductive pads 34, for establishing electrical connectivity between cover 10 (not shown) and the analyzer instrument 2. FIG. 4, also shows electrically conductive pads 40, 42 and 44 and other features described with reference to FIG. 3.

Figure 5:
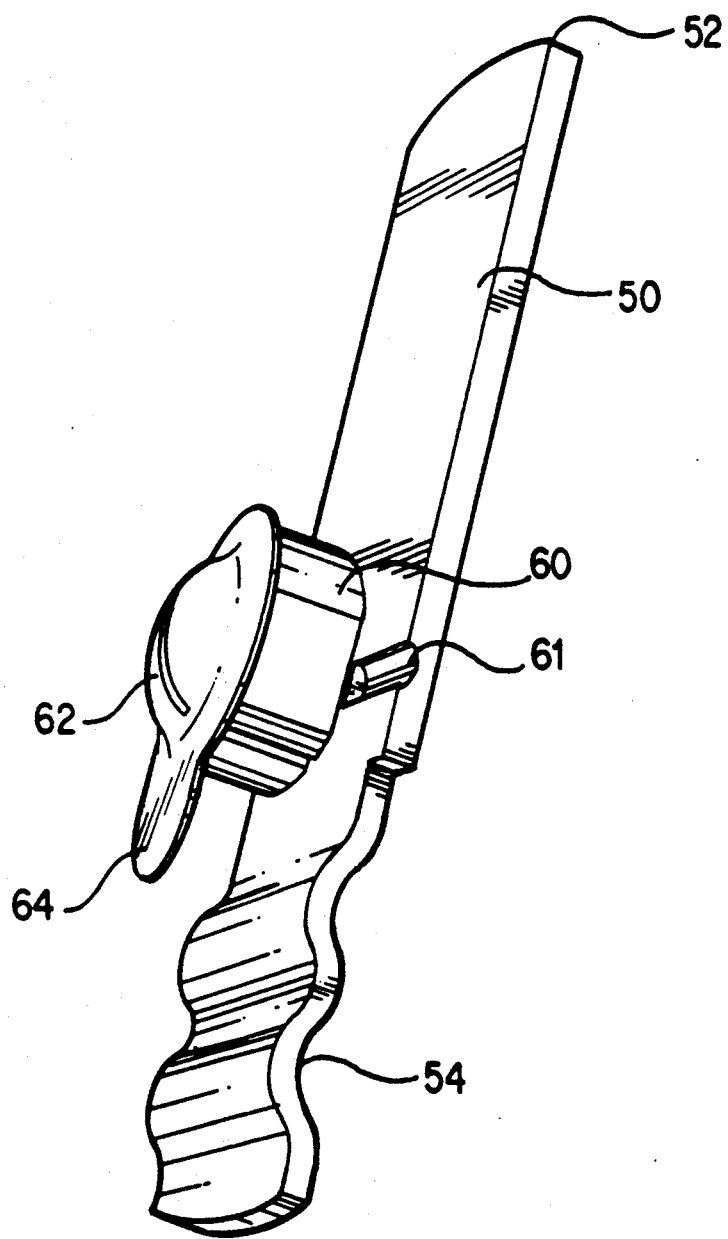
FIG. 5 is a side view showing the top of the sensor unit of the system of the present invention.

FIG. 5 depicts, in top view, a disposable sensor unit, 50, for use in the system of the present invention. The leading edge 52, of sensor unit 50 is rounded to facilitate the insertion of the sensor unit into the receiving portion of the analyzer instrument. Trailing edge 54, of sensor unit 50, is molded with ridges that facilitate the gripping and holding of the sensor unit by a user of the system. The indentation 61 forms a notch on the top surface of the sensor unit that provides means for mechanically engaging corresponding means in the analyzer instrument, such as detent springs, when the sensor unit is fully inserted into the analyzer instrument. Although not shown in FIG. 5, the top surface of the sensor unit may contain an additional notch located on the side of the top surface of the sensor unit opposite the side containing notch 61.

In FIG. 5, ion selective electrode 60, is depicted with cover 62, in place. As previously described, cover 62 is adapted, with portion 64, to be peeled off to permit the placement of a fluid sample in contact with the ion selective electrode. The peel-off cover, or cap 62, acts as a moisture barrier and thereby prevents evaporation of a hydrogel placed over the ion selective electrode. Preferably the peel-off cap is formed from a polymer-coated aluminum sheet that, in addition to acting as a moisture barrier, pulls the hydrogel off the ion sensitive electrode, as the cap is peeled away from the ion sensitive electrode. In this manner, peeling the cap off the ion sensitive electrode removes the hydrogel and exposes the electrode for sample deposition. A further advantage of the polymer-coated aluminum cap is that the cap generally will not react electrochemically with salt solutions in the hydrogel.

Figure 6:
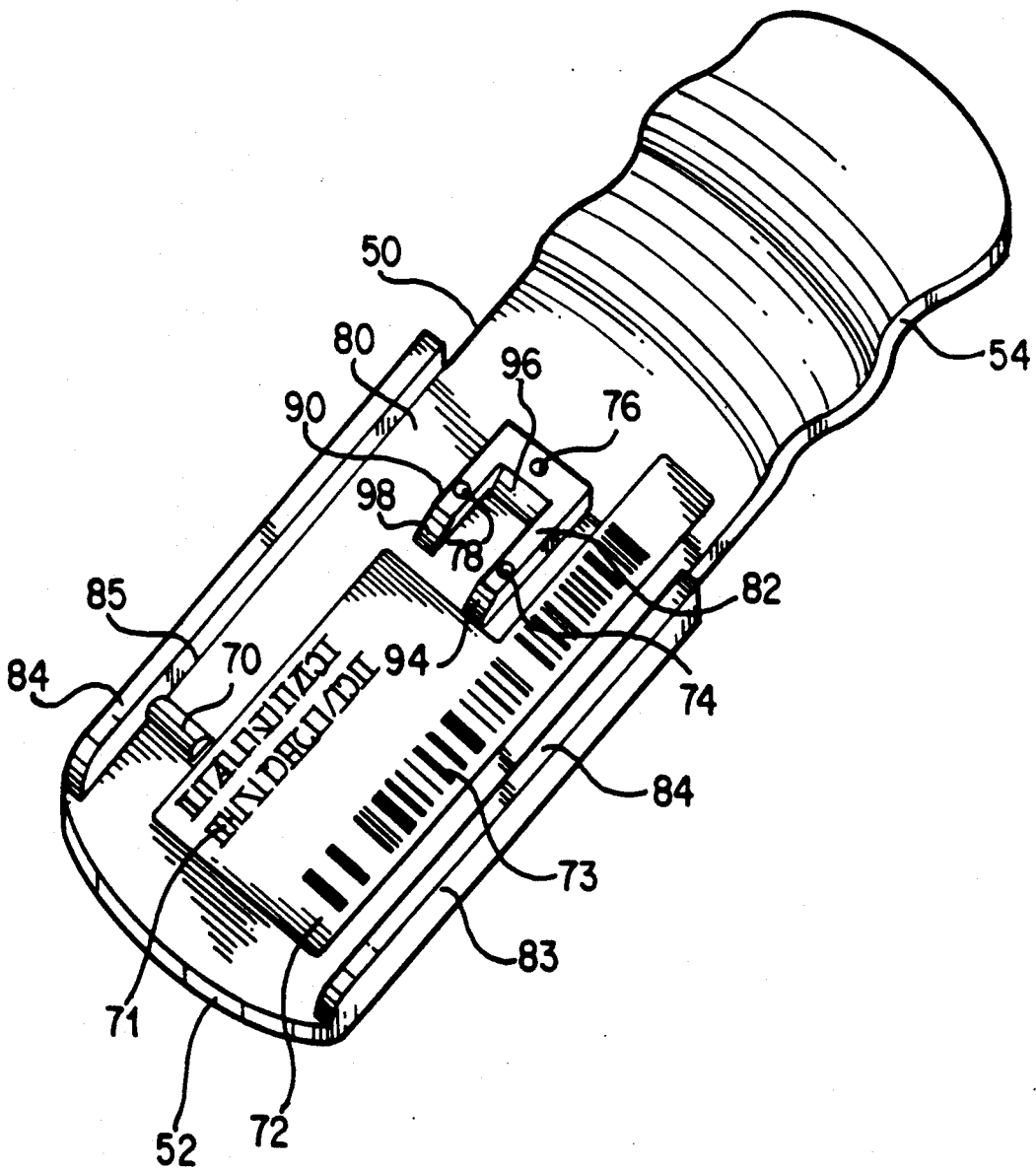
FIG. 6 is a bottom view of the sensor unit of the system of the present invention.

FIG. 6 depicts a bottom view of the sensor unit of the present invention. When viewed from below as in FIG. 6, planar surface 80, containing label 72, is below the level of planar surface 82, containing electrical contacts 74, 76 and 78 that extend through the sensor unit and electrically communicate with the ion selective electrode. Planar surface 82 forms the upper surface of platform 90. The sloped surfaces 94, 96 and 98 of platform 90, located between the leading edge 52 of the sensor unit and electrical contacts 74, 76 and 78 respectively are ramped, i.e. each slopes towards the leading edge 52. The ramping allows electrical contacts 110, 112 and 114, shown in FIG. 8, to be depressed as the sensor unit is being inserted into the analyzer instrument. The advantages of depressing the electrical contacts during insertion of the sensor unit into the analyzer instrument are set forth above.

Planar surface 84, of the bottom of sensor unit 50, is raised above the level of planar surface 82, in the view of sensor unit 50 depicted in FIG. 6. Planar surface 84, forms the top surface of elevating means 83 and 85. Elevating means 83 and 85 may comprise perpendicular rail sections, perpendicular to the bottom surface 80, of sensor unit 50, formed from the plastic or polymeric material utilized to form the sensor unit. Planar surface 84 comprises the sliding surface of the sensor unit that contacts the receiving portion of the analyzer instrument when the sensor unit is inserted into the analyzer instrument. As set forth above, preferably, planar surface 84 may be fabricated from an electrically conductive material or coated with an electrically conductive material. Utilizing rails 83 and 85 to elevate planar surface 84 advantageously reduces the area of contact between the analyzer instrument and the sensor unit and thereby minimizes the generation of static electricity.

Figure 12:
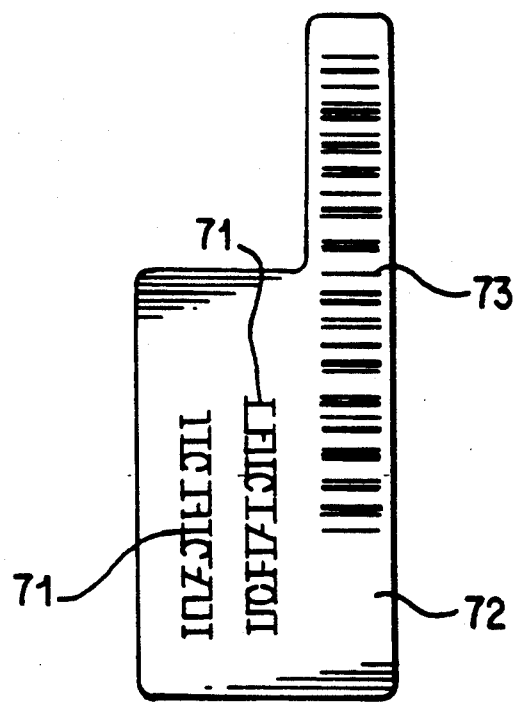
FIG. 12 is a view of a label that may be utilized on the sensor unit of the system of the present invention.

Label 72, shown in FIG. 6 may be utilized to record information such as sensor lot number, expiration date and electrochemical performance. As shown in FIG. 6, label 72 may contain information in bar code format 73, and/or written information 71. As also shown in FIG. 6, label 72 may be adapted to fit around platform 90. Label 72, is shown apart from the sensor unit in FIG. 12. As will be understood by those of ordinary skill in the art label 72 may be a conventional adhesive label, or alternatively, the information 71 and 73 contained on label 72 may be printed directly on the bottom surface 80, of sensor unit 50.

The raised portion of bar 70 is depicted in FIG. 6. Bar 70 may be utilized to engage the actuation mechanism in the receiving portion of the analyzer instrument.

Figure 7:
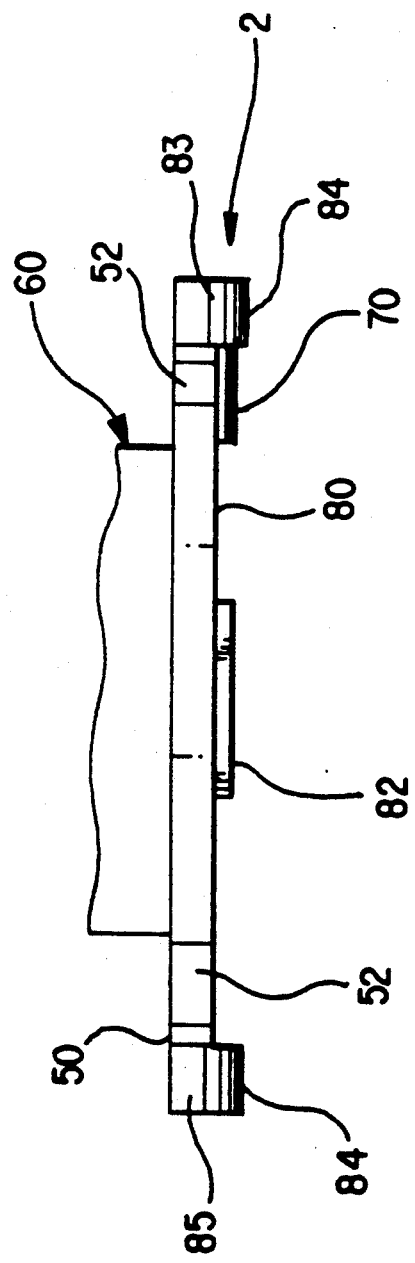
FIG. 7 is a side view of part of the sensor unit of the system of the present invention.

FIG. 7 depicts a side view, from the leading edge 52 of sensor unit 50 showing the spatial relationship between planar surfaces 80, 82 and 84 and bar 70 utilized to mechanically engage the actuating means in the receiving unit. A portion of ion selective electrode 60 is also depicted.

Figure 8:
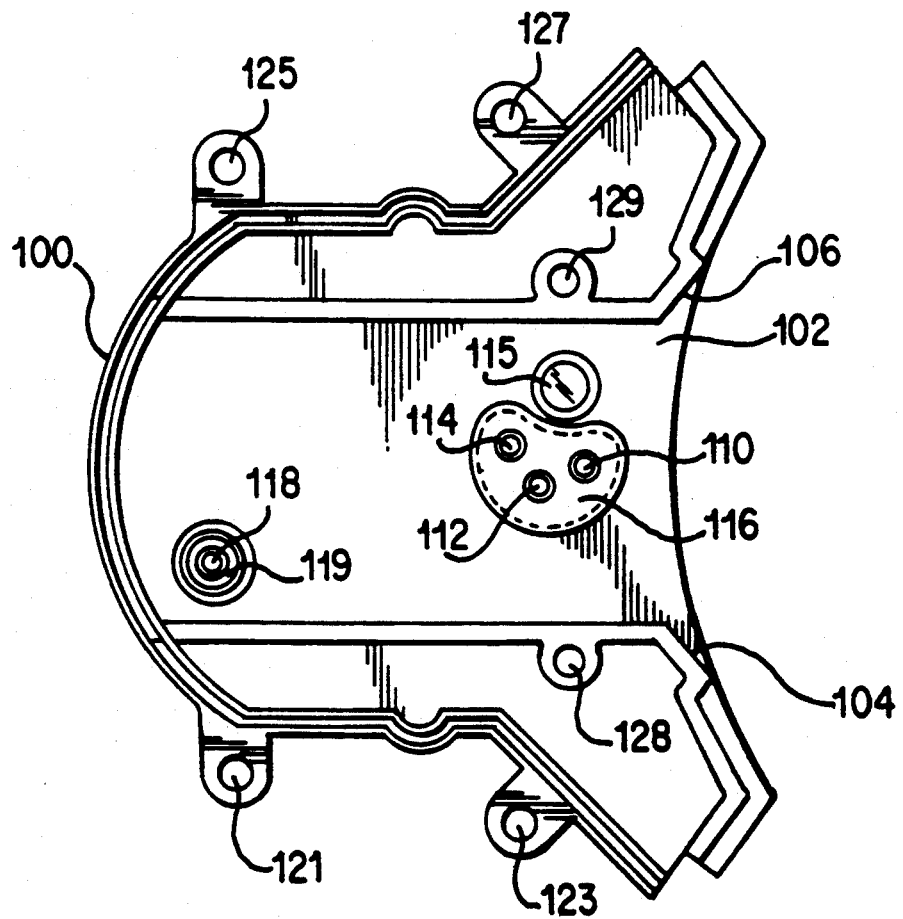
FIG. 8 is a top view of the lower surfaces of the receiving portion of the analyzer instrument of the system of the present invention.

FIG. 8 depicts a top view of the receiving portion, 100 of the analyzer instrument. This portion of the analyzer instrument is adapted to receive a sensor unit. The sensor unit would be inserted in the direction indicated by the arrow. As shown in FIG. 8, receiving portion 100, may be fabricated to include guiding surfaces 104 and 106 to guide and facilitate positioning the sensor unit during its insertion. The sliding surface of the sensor, 84 in FIGS. 6 and 7, would slide along sensor slide surface 102 in FIG. 8. As explained in a preceding section, the sensor slide surface may be fabricated from an electrically conductive material, or may be coated with an electrically conductive material.

Electrically conductive pads, or contacts, 110, 112 and 114 may be resiliently mounted and are positioned in elastomeric membrane 116 in a location such that when the sensor unit 50 is fully inserted into the analyzer instrument, electrically conductive pads 110, 112 and 114 are located directly below electrical contacts 76, 78 and 74 respectively. As set forth above, when sensor unit 50 is fully inserted, platform 82, carrying electrical contacts 74, 76, and 78, is in position to establish electrical communication between contacts 76, 78 and 74 of the sensor unit and electrically conductive pads 110, 112 and 114 of the receiving unit. Electrically conductive pads 110, 112 and 114 are electrically connected to the circuitry in the analyzer instrument that analyzes the electrical signals from the ion selective electrode and determines the ion level of the fluid sample. The electrical communication between pads 74, 76 and 78 of the sensor unit and electrically conductive pads 110, 112 and 114 of the receiving portion, completes an electrical circuit between the ion selective electrode and the analyzer circuitry. The transparent window, 115, for the bar code reading unit, is positioned in a location that enables the bar code on the bottom surface of the sensor unit to be read as the sensor is inserted into the analyzer instrument. The bar code reading unit is fixed in the analyzer instrument beneath the transparent window 115. The bar code reading unit of the present invention may be a conventional unit known to those of ordinary skill in the art. Suitable bar code reading units for use in the present invention are commercially available from companies such as Hewlett-Packard.

When the sensor unit 50, is fully inserted, bar 70 on the sensor unit contacts and depresses, microswitch actuator 118 mounted in an elastomeric membrane 119. The depression of the microswitch actuator 118, signals the analyzer instrument circuitry that the sensor unit 50 is fully inserted.

The receiving portion 100, may be mounted in the analyzer instrument housing in any manner known to the art. FIG. 8 depicts, mounting holes 121, 123, 125, 127, 128 and 129 through which fastener means, such as screws, may be inserted to position and hold the receiving portion 100 in the analyzer instrument.

Figure 9A:
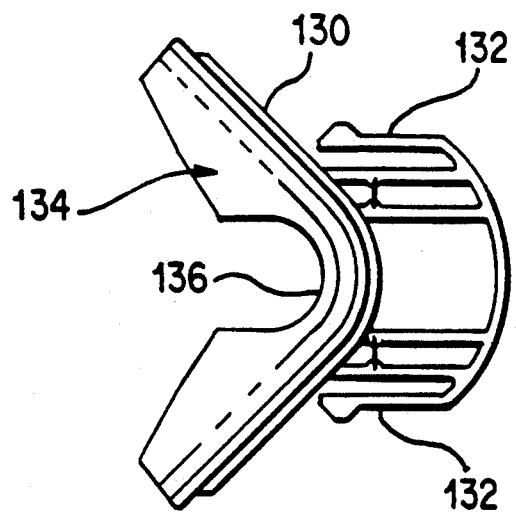
FIG. 9a is a top view of a removable part of an analyzer slide for use in the analyzer instrument of the system of the present invention.
Figure 9B:
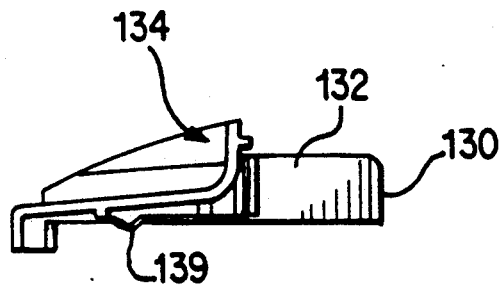
FIG. 9b is a side view of a removable part of an analyzer slide for use in the analyzer instrument of the system of the present invention.
Figure 9C:
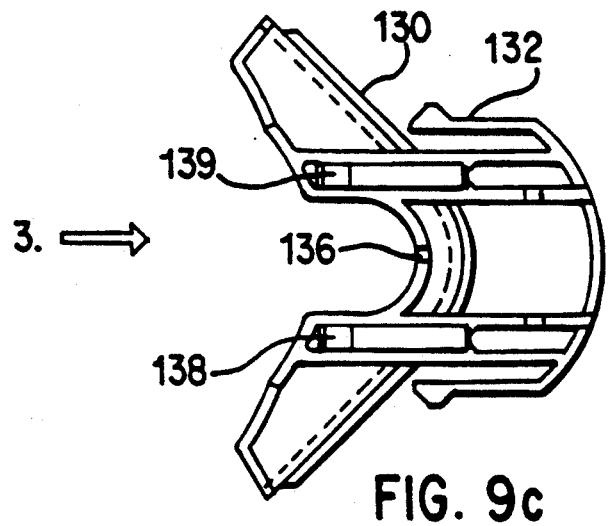
FIG. 9c is a bottom view of a removable part of an analyzer slide for use in the analyzer instrument of the system of the present invention.

As discussed in a preceding section, receiving portion 100 of the analyzer instrument may include a removable analyzer slide portion. FIGS. 9a, 9b and 9c show removable analyzer slide portion, 130 in top view, side view and bottom view respectively. Detent springs 132, may be utilized to secure the removable analyzer slide 130 in receiving portion 100 of the analyzer instrument. Electroconductive surface 134, contacts the sensor unit during its insertion into the receiving portion. Electroconductive surface 134 may be fabricated from an electroconductive material, or may be fabricated with a non-electroconductive material and coated with an electroconductive material. Analyzer slide portion, 130 is fabricated with a cut-out portion 136 that corresponds to the outer dimensions of the ion selective electrode on sensor unit 50. As shown in FIG. 9c, analyzer slide portion 130 may be equipped with detent springs 138 and 139, or similar means, for mechanically communicating with, and positioning sensor unit 50 after its insertion into the analyzer instrument. For example, detent springs 138 and 139 may mechanically communicate with notch 61 and a similar notch near the other side of the top surface of the sensor unit. The relative positions of receiving portion 100, and removable slide portion 130, may be ascertained from FIG. 14.

Figure 10A:
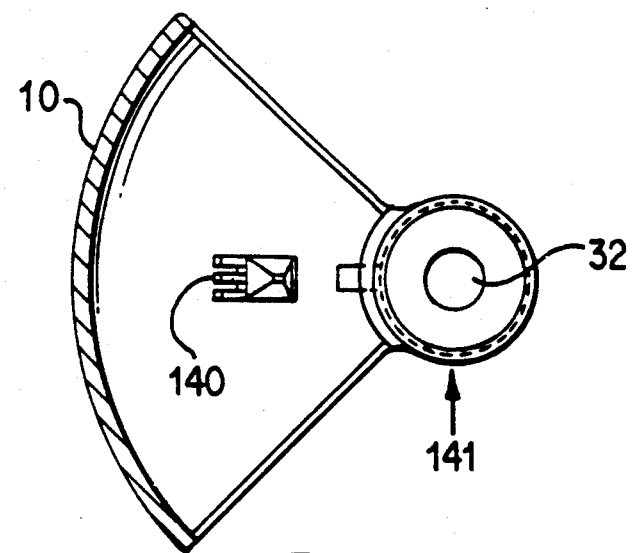
FIG. 10a is a bottom view of the inside of a door for use in the analyzer instrument of the system of the present invention.
Figure 10B:
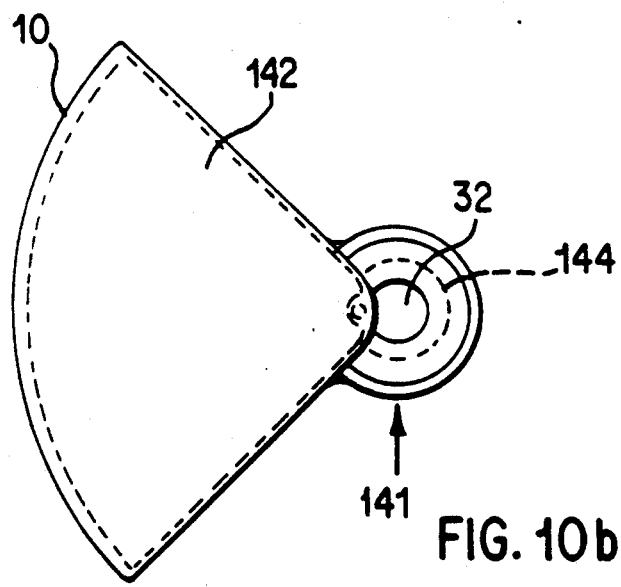
FIG. 10b is a top view of a door for use in the analyzer instrument of the system of the present invention.
Figure 10C:
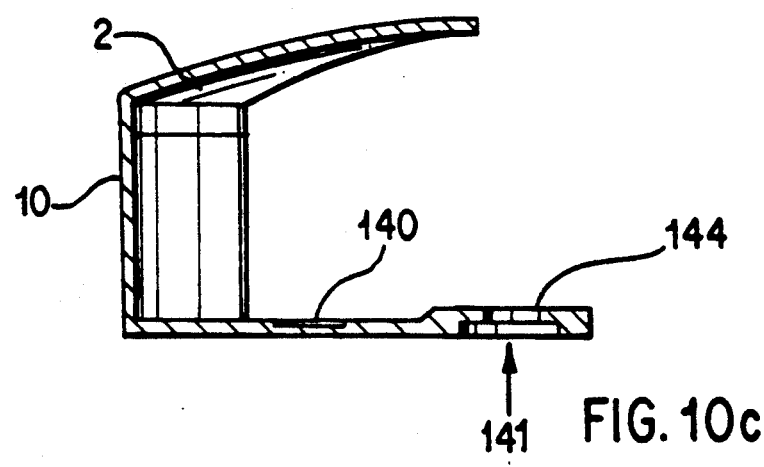
FIG. 10c is a side view of a door for use in the analyzer instrument of the system of the present invention.

FIGS. 10a, 10b and 10c depict a bottom (inside) view, top (outside) view and cross-sectional view of cover, or door, 10 that is slideably mounted on the analyzer instrument and used to cover the receiving portion of the analyzer instrument and pivots around pivot axis 141. As shown in FIG. 10a, cover, or door, 10 is equipped with electrically conductive bar, or spring 140 that electrically communicates with electrical contacts 40 and 42, shown in FIGS. 3 and 4, when door 10 is in the closed position. As shown in FIG. 10b, cover, or door, 10 is fabricated in a manner so as to contain electroconductive shield material 142. Circular conductive area 144, electrically communicates with raised sliding contact 30, shown in FIG. 3, or raised electrical contacts, or pads, 34 shown in FIG. 4.

Figure 11A:
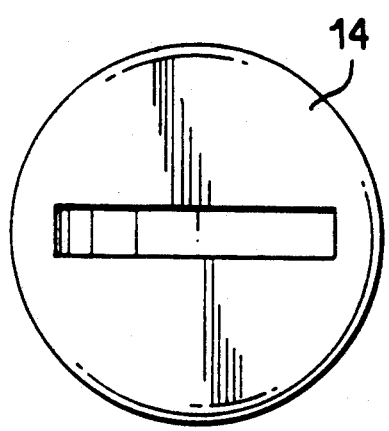
FIG. 11a is a top view of a pivot screw for use in the analyzer instrument of the system of the present invention.
Figure 11B:
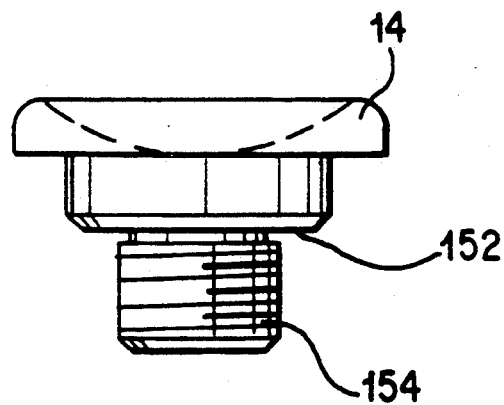
FIG. 11b is a side view of a pivot screw for use in the analyzer instrument of the system of the present invention.

FIGS. 11a and 11b depict a top and side view of a pivot screw that may be utilized to pivotly fasten cover 10 to the analyzer instrument. Pivot screw 14, comprises threaded portion 154, and a shoulder portion 152 that prevents it from being over tightened. Pivot screw 14 is mounted through hole 32 shown in FIGS. 3, 4, 10a and 10b.

Figure 13A:
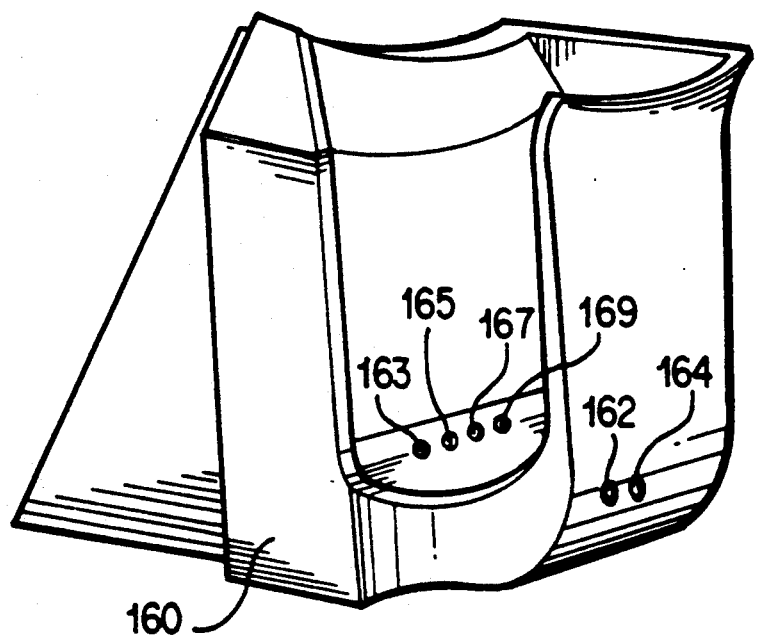
FIG. 13a is a front quarter view of one side of the recharger unit of the system of the present invention.
Figure 13B:
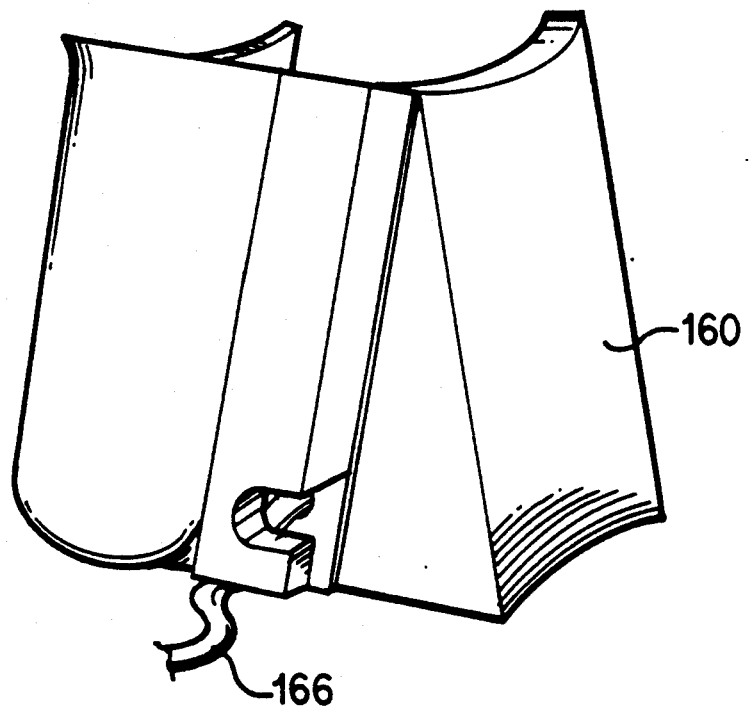
FIG. 13b is a rear quarter view of one side of the recharger unit of the system of the present invention.

FIGS. 13a and 13b depict a rechanger unit 160 for use in the system of the present invention. Recharger unit 160 is adapted to receive and hold a portion of analyzer instrument 2. When analyzer instrument 2, is inserted into recharger unit 160, electrical contacts 163, 165, 167 and 169 are positioned adjacent to, and electrically communicate with, electrical contacts 3, 5, 7 and 9 in the analyzer instrument housing to complete a recharging circuit. This recharging circuit, when connected to a source of AC power, allows the rechargeable batteries in the analyzer instrument to be recharged. Light emitting diodes (LED's) 162 and 164 are provided in the recharger unit housing for indicating power and recharge rate status. As will be understood by those of ordinary skill in the art, LED's 162 and 164 electrically communicate with the recharger circuitry.

Electrical cord, 166 is utilized to contact the recharger unit 160, to a source of AC power. As will be understood by those of ordinary skill in the art, recharger unit 160 contains conventional electronic means for converting AC power to direct current for recharging rechargeable batteries. When the analyzer instrument 2, is inserted into recharger unit 160, and recharger unit 160 is connected to a source of AC power through electrical cord 166, recharging of the analyzer instrument batteries occurs through the recharging circuit.

Figure 14:
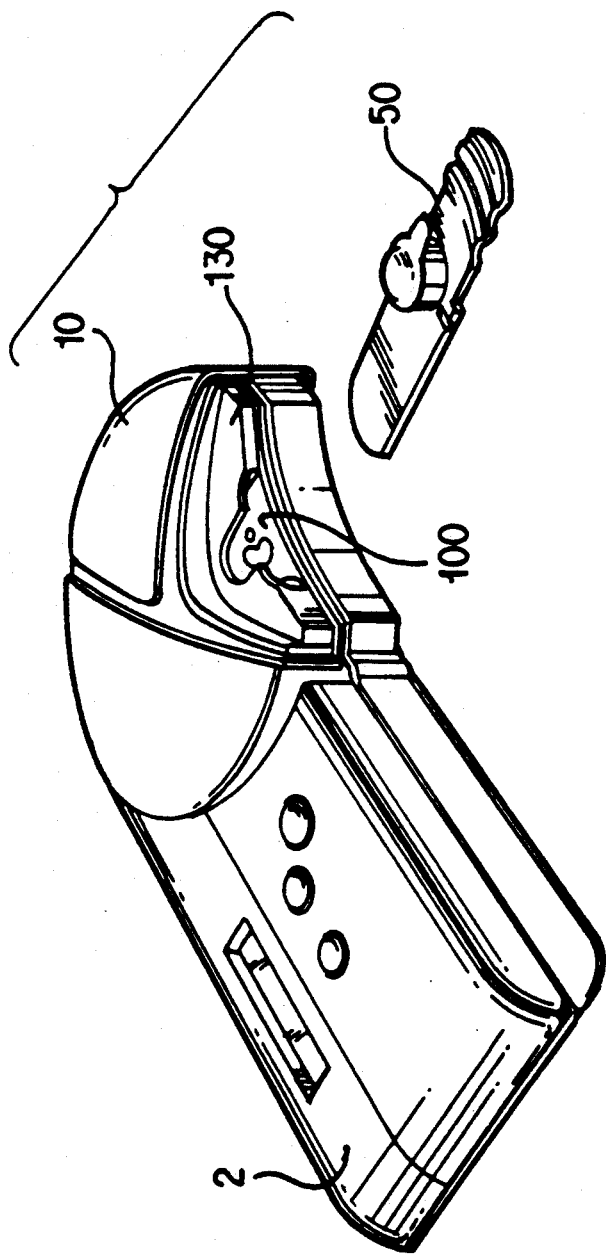
FIG. 14 is a view of the analyzer instrument, with the door in the open position, and the sensor unit of the system of the present invention.

FIG. 14 depicts analyzer instrument 2, with cover, or door, 10 in the open position for receiving sensor unit 50. As shown in FIG. 14, receiving portion 100 and analyzer slide 130, which in this view is fully inserted into analyzer instrument 2, may be viewed through the open cover, and are accessible for cleaning.

The use of the system of the present invention will be readily understood by those of ordinary skill in the art. To use the system of the present invention to detect ion level in a fluid sample, assuming the batteries that power the analyzer circuitry in the analyzer instrument have been sufficiently charged, the analyzer instrument is turned on by pushing switch 26. Following instructions displayed on the analyzer display means 30, the sensor unit 50 is inserted leading edge 52 first, into receiving portion 100 of analyzer instrument 2, cover 10 having first been moved to the open position. When sensor unit 50 is fully inserted into receiving portion 100, cover 10 is moved to the closed position to completely enclose sensor unit 50 within the housing of analyzer instrument 50. As set forth above, when sensor unit 50 is fully inserted into analyzer instrument 2, bar 70 on the sensor unit contacts microswitch actuator 118 of receiving portion 100 which informs the analyzer instrument circuitry that the sensor unit is fully inserted. Also as set forth above, cover, or door, 10 is equipped with electrically conductive bar 140 that upon fully closing the cover, contacts electrical contacts 40 and 42 located in the bottom of the receiving portion which informs the analyzer instrument circuitry that cover, or door, 10 is fully closed.

The full insertion of sensor unit 50 into analyzer instrument 2, causes electrical contacts 74, 76 and 78, on the sensor unit, to contact and electrically communicate with electrically conductive pads 110, 112 and 114 of the receiving portion of the analyzer instrument thereby completing an electrical circuit. The analyzer instrument circuitry is then precalibrated based on the specific ion selective electrode of the sensor unit.

The analyzer will indicate on display 20 when preliminary sensor calibration has been completed and the sensor unit is ready to accept a fluid sample. Cover 10 is moved to the open position and the peel-off cover 62 is removed from ion selective electrode 60 by pulling on tab 64. The removal of cover 62 removes a hydrogel layer that covers the ion selective electrode. If desired the sensor unit may be removed from the analyzer instrument before removing peel-off cover 62.

After removal of peel-off cover 62, a fluid sample is placed on ion selective electrode 60 and then sensor unit 50, if removed for deposition of the fluid sample, is re-inserted, into the analyzer instrument. The door 10 is then closed. The analyzer instrument will then analyze the electrical output from the ion selective electrode and determine the ion level in the fluid sample. The ion level will be displayed in display means window 20.

As will be understood by those of ordinary skill in the art, ion selective electrodes, and analyzer circuitry exist for determining the ion levels of a variety of ions including, potassium ions and calcium ions. With the appropriate ion selective electrode and appropriate modifications to the analyzer instrument circuitry, the system of the present invention may be utilized to determine the ion level in a fluid sample of a variety of ions.

We claim:

1. A system for analyzing the ion level of a fluid sample comprising:
    an analyzer instrument containing electrical circuitry for analyzing the ion level of the fluid sample and a receiving portion;
    a sensor unit, adapted to communicate with the receiving portion of the analyzer instrument, wherein said sensor unit comprises
        a substantially planar member having an upper and a lower surface, and a leading edge adapted for insertion into said analyzer instrument and a trailing edge adapted for gripping by a user's hand;
        notches in the upper surface of the member to mechanically engage the analyzer instrument when the sensor unit is fully inserted into the analyzer instrument;
        an ion selective electrode in communication with the upper surface of the member and the fluid sample;
        a label affixed to the lower surface of the member;
        substantially perpendicular rails in communication with the side edges of the lower surface of the member, being of equal depth to form a first substantially planar surface that is substantially parallel to the lower surface of the member and is disposed beneath the lower surface of the member; wherein said first substantially planar surface is adapted to mechanically contact the receiving portion of the analyzer instrument upon insertion into the analyzer instrument; and
        electrical contacts in communication with the ion selective electrode, that communicate with the analyzer instrument upon insertion of the sensor unit into the analyzer instrument, said electrical contacts extending through said member to the lower surface of the member to an equal depth beneath the lower surface to form a second substantially planar surface, having a leading edge and a trailing edge, and disposed between the lower surface of the member and the first substantially planar surface;
    and wherein actuating means are provided in the receiving portion of the analyzer instrument for informing the analyzer instrument that the sensor unit is in position.

2. The system of claim 1 wherein the analyzer instrument comprises:
    resiliently mounted electrical contacts for receiving electrical output from the ion sensitive electrode;
    electrical circuitry for analyzing electrical output from the ion sensitive electrode;
    a display for displaying the ion level of the fluid sample being analyzed; and
    a power source for the electrical circuitry and the display.

3. The system for analyzing the ion level of fluid sample according to claim 2, wherein said analyzer instrument is battery-operated, and said analyzing system further comprises a recharger means for recharging said analyzer instrument.

4. The system for analyzing the ion level of fluid sample according to claim 1, wherein said actuating means in the receiving portion of the analyzer instrument engages a bar provided in the lower surface of the sensor unit.

5. The system for analyzing the ion level of fluid sample according to claim 1, wherein the leading edge of said second substantially planar surface slopes towards the leading edge of the sensor unit at an angle to contact said first substantially planar surface.

6. The system for analyzing the ion level of fluid sample according to claim 1, wherein said ion selective electrode is covered with a hydrogel.

7. The system for analyzing the ion level of fluid sample according to claim 6, further comprising a peel-off cap provided over the hydrogel to act as a moisture barrier.

8. The system for analyzing the ion level of fluid sample according to claim 7, wherein said peel-off cap is formed from a polymer-coated aluminum sheet.

9. The system for analyzing the ion level of fluid sample according to claim 1, wherein said receiving portion of the analyzer instrument is provided with guiding means for receiving the sensor unit.

10. The system for analyzing the ion level of fluid sample according to claim 9, wherein said guiding means include detent springs that bear down on the upper surface of the sensor unit.

11. The system for analyzing the ion level of fluid sample according to claim 10, wherein said detent springs engage said notches on the sensor unit.

12. The system for analyzing the ion level of fluid sample according to claim 9, wherein said guiding means is provided with an electroconductive coating to reduce electrostatic.

13. The system for analyzing the ion level of fluid sample according to claim 9, wherein said guiding means are removable to facilitate cleaning.

14. The system for analyzing the ion level of fluid sample according to claim 1, wherein the sensor unit is provided with an electroconductive coating to reduce electrostatic.

15. The system for analyzing the ion level of fluid sample according to claim 1, wherein said receiving portion of the analyzer member is provided with a sensor slide surface.

16. The system for analyzing the ion level of fluid sample according to claim 15, wherein said sensor slide surface is provided with an electroconductive coating to reduce electrostatic.

17. The system for analyzing the ion level of fluid sample according to claim 15, wherein said sensor slide surface is removable to facilitate cleaning.

18. The system for analyzing the ion level of fluid sample according to claim 15, wherein said sensor sliding surface is made of polyvinyl chloride.

19. The system for analyzing the ion level of fluid sample according to claim 1, wherein said actuating means is an electrical switch.

20. The system for analyzing the ion level of fluid sample according to claim 1, wherein said receiving portion of the analyzer instrument is provided with a cover.

21. The system for analyzing the ion level of fluid sample according to claim 20, further comprising electrical means for detecting when the cover is fully closed.

22. The system for analyzing the ion level of fluid sample according to claim 1, wherein the ion selective electrode has less than 300 MegOhm resistance, measured using a 100 pico amp current.

* * * * *

UNITED STATES PATENT AND TRADEMARK OFFICE
CERTIFICATE OF CORRECTION

PATENT NO. : 5,221,457
DATED : June 22, 1993
INVENTOR(S) : John R. North et al

It is certified that error appears in the above-indentified patent and that said Letters Patent is hereby corrected as shown below:

| Column | Line | |
|--------|------|---|
| 1 | 26 | After "film" change "," to --.--. |
| 4 | 4 | After "hydrogels" delete ",". |
| 4 | 62 | After "portion" delete "of the analyzer instrument". |
| 7 | 12 | Change "a" to --an--. |
| 7 | 37 | After "display means" delete ",". |
| 8 | 44 | After "above" insert --,--. |
| 8 | 46 | After "section" insert --,--. |
| 9 | 18 | Change "electrically" to --electricity--. |
| 10 | 63 | After "switches" delete ",". |

UNITED STATES PATENT AND TRADEMARK OFFICE
CERTIFICATE OF CORRECTION

PATENT NO. : 5,221,457
DATED : June 22, 1993
INVENTOR(S) : John R. North et al

It is certified that error appears in the above-indentified patent and that said Letters Patent is hereby corrected as shown below:

| Column | Line | |
|---|---|---|
| 11 | 26 | After "FIG. 3" delete ",". |
| 11 | 28 | Change "a" to --an--. |
| 11 | 49 | After "comprise" delete "a raised". |
| 13 | 5 | After "50" insert --,--. |
| 14 | 30 | After "spring" insert --,--. |
| 14 | 40 | Change "pivotly" to --pivotably--. |
| 14 | 62 | After "cord" delete ","; change "contact" to --connect--. |

Signed and Sealed this

Twenty-fifth Day of October, 1994

Attest:

BRUCE LEHMAN

*Attesting Officer*     *Commissioner of Patents and Trademarks*